United States Patent [19]

Beck et al.

[11] Patent Number: 5,977,458
[45] Date of Patent: Nov. 2, 1999

[54] CORN INBRED LINES FOR DAIRY CATTLE FEED

[75] Inventors: James F. Beck, Marshall, Mich.; Dale H. Storck, Sugar Grove, Ill.

[73] Assignee: Cargill Incorporated, Wayzata, Minn.

[21] Appl. No.: 09/136,912

[22] Filed: Aug. 20, 1998

Related U.S. Application Data

[62] Division of application No. 08/641,486, May 1, 1996, Pat. No. 5,859,353.

[51] Int. Cl.$^6$ ............... A01H 5/00; A01H 4/00; A01H 1/00; C12M 5/04
[52] U.S. Cl. ............ 800/320.1; 800/298; 800/275; 800/271; 435/412; 435/424; 435/430; 435/430.1
[58] Field of Search ................ 800/320.1, 298, 800/275, 271; 435/412, 424, 430, 430.1

[56] References Cited

U.S. PATENT DOCUMENTS 5,145,695  9/1992  Smith et al. .
5,219,596  6/1993  Smith et al. .

OTHER PUBLICATIONS

Barriere et al., *Agronomie*, 13:865–876, 1993.
Block et al., *J. Dairy Sci.*, 64:1813–1825, 1981.
Frenchick et al., *J. Dairy Sci.*, 59:2126–2129, 1976.
Goering et al., *Agricultural Handbook*, 379:1–20, 1975.
Grant et al., *J. Dairy Sci.*, 78:1970–1980.
Keith et al., *J. Dairy Sci.*, 62:788–792, 1979.
Rook et al., *J. Dairy Sci.*, 60:1894–1904, 1977.
Sommerfield et al., *J. Dairy Sci.*, 62:1611–1618, 1979.
Stallings et al., *J. Dairy Sci.*, 65:1945–1949, 1982.
Weller et al., *J. Agric. Sci. Camb.*, 106:31–35, 1986.
Barriere et al., *Bull. Tech. C.R.Z.V. Theix*, 60:43–58, 1985.

*Primary Examiner*—Gary Benzion
*Attorney, Agent, or Firm*—Fish & Richardson, P.C.

[57] ABSTRACT

An inbred corn line designated AR5651bm3 is disclosed. AR5651bm3 is useful for priducing $F_1$ hybrid corn seed and plants therefrom. Such corn plants exhibit the brown midrib phenotype and yield a silage that, when fed to dairy cattle, increases milk production.

8 Claims, No Drawings

CORN INBRED LINES FOR DAIRY CATTLE FEED

This application is a divisional of U.S. application Ser. No. 08/641,486, filed May 1, 1996, now U.S. Pat. No. 5,859,353.

FIELD OF THE INVENTION

This invention relates to corn inbred lines and the feeding of corn silage for lactating dairy cattle. More particularly the invention relates to a dairy cattle feed ration comprising silage from corn plants exhibiting the brown midrib phenotype.

BACKGROUND OF THE INVENTION

Breeding of Corn Plants

Corn plants (*Zea mays* L.) are bred by both self-pollination and cross-pollination techniques. Corn is a monoecious plant, i.e., each plant has separate male and female flowers on the same plant, located on the tassel and ear, respectively. Natural pollination occurs in corn when pollen is shed from tassels and contacts silks of the same plant or a different plant that protrude from tops of the developing ears. Methods and techniques for the development of inbred corn lines and hybrid corn varieties are known in the art. Hallauer, A., Maize, in Principles of Cultivar Development, Vol. 2, Fehr. W. ed. pp. 249–294, Macmillan, New York, (1987). Currently, many hybrid corn varieties are produced by crossing two inbred lines to produce $F_1$ hybrid progeny. The $F_1$ plants exhibit heterosis, or hybrid vigor, resulting in plants having high yield and superior agronomic performance in the hybrid combination. The production and development of inbred corn lines and hybrid corn varieties are discussed in, for example, U.S. Pat. No. 5,367,109, which is incorporated herein by reference.

Research studies on maize have resulted in the identification of numerous genetic loci. See, e.g., the maize genetic database on the Worldwide Web at http://teosinte.agron.missour.edu/top.html.

To supply the need nutrients for increased milk production by lactating dairy cattle is an ongoing challenge facing the dairy industry. This challenge is complicated by the fact that, even though a dairy cow's diet may meet the National Research Council recommended nutrient requirements, the diet may still lack some nutrients at increased levels required for higher milk production. One reason for this difficulty in meeting nutrient requirements is the complexity of the digestive system of ruminants such as dairy cattle.

In cattle, ingested feed first passes into the reticulorumen, where it is subject to anaerobic microbial fermentation. Microbial fermentation begins the digestive process and gives a ruminant the ability to utilize fibrous feeds, in contrast to monogastric animals. Ruminants meet their nutrient needs by utilizing the by-products of microbial fermentation, along with any undigested feed residues and the resultant microbial mass that passes from the rumen.

Anaerobic microbial fermentation is an advantage to ruminants because it allows them to benefit from feeds which cannot be utilized by non-ruminants. However, microbial activity limits the ability to provide supplemental nutrients to a ruminant animal, because many desirable nutrients, such as proteins, amino acids and digestible fiber, will be metabolized by microbes before the nutrients reach a site where they can be absorbed and utilized by the ruminant.

Attempts have been made to increase milk production in dairy cattle by manipulating the feed ration. For example, rations containing silage derived from corn plants carrying a brown midrib mutation have been fed to cattle. Stallings, C. et al., J. Dairy Sci., 65:1945–1949 (1982); Block, E. et al., J. Dairy Sci. 64:1813–1825 (19:31); Keith, E. et al., J. Dairy Sci. 62:788 (1979). The bm gene decreases and alters the lignin content in the vegetative parts of such corn plants; silage made from such plants has increased fiber digestibility compared to silage from corn plants not exhibiting the brown midrib phenotype. In general, these studies indicated that there was no increase in milk production in cows fed silage from bm corn. It was concluded that the cows fed a diet containing bm silage partitioned the nutrients into meat or fat body tissues rather than milk production. Barriere et al., Agronomie 13:865–876 (1993).

Attempts have been made to increase the efficiency of feed utilization and milk production by using various formulations and feed supplements. Despite continued improvement in the development of dairy cattle feed rations, it is desirable to further increase the efficiency of feed utilization and milk production by dairy cattle,

SUMMARY OF THE INVENTION

Inbred corn seed is disclosed herein. Inbred corn seeds of the invention include seed designated AR5252bm3, AR5251bm3, AR5651bm3, AR5551bm3, AR5153bm3, AR5253bm3 and AR5654bm3.

Also disclosed herein is hybrid corn seed that is produced from plants of any one of the above inbred corn line, which has been crossed to plants of a second inbred line that is homozygous for bm3.

An $F_1$ hybrid corn plant is disclosed herein. An $F_1$ corn plant of the invention is produced by planting and growing seeds of a first corn inbred line selected from the above-identified inbred lines, i.e., AR5252bm3, AR5251bm3, AR5651bm3, AR5551bm3, AR5153bm3, AR5253bm3 and AR5654bm3. These seeds are planted in proximity to seeds of a second inbred line that is homozygous for bm3, so that natural pollination between plants of the two inbred lines can take place. Pollen production is prevented on plants of the first inbred line or on plants of the second inbred line, e.g., by removal of tassels prior to pollen production. Natural cross pollination then is allowed to occur between the inbred line plants which are producing pollen and the inbred line plants which have had pollen production prevented. Seeds are produced on the plants which have had pollen production prevented and these seeds are harvested. At least one of the harvested seeds is then grown into a plant.

An article of manufacture is disclosed herein, which comprises packaging material, a substantially homogenous assemblage of $F_1$ hybrid corn seeds within the packaging material and a package label accompanying the packaging material. The seeds within the packaging material are homozygous for at least one bm locus, i.e., a brown midrib locus. The package label indicates that the seeds within the package are suitable for producing plants that yield a silage that can be used in the feeding of dairy cattle. The seeds can be homozygous for bm3. The seeds may be produced by hybrid combination of plants from a first corn inbred line selected from the above-identified lines, i.e., AR5252bm3, AR5251bm3, AR5651bm3, AR5551bm3, AR5153bm3, AR5253bm3 and AR5654bm3 and plants of a second inbred line that is homozygous for bm3.

DESCRIPTION OF THE PREFERRED EMBODIMENTS

A dairy cattle feed ration has been discovered that comprises a corn silage produced from corn plants exhibiting a brown midrib phenotype; feeding of such silage to dairy cattle results in unexpected improvements in milk production.

A silage component is produced from corn plants displaying the brown midrib phenotype. This phenotype is exhibited by plants homozygous for a mutant allele at either the bm1, bm2, bm3 or bm4 locus. In some embodiments, such plants may display the brown midrib phenotype due to homozygosity at more than one of the bm loci. Mutant bm alleles are known to reduce and alter the lignin content in plants homozygous for such alleles. The lignin content may be reduced 20%, 30%, or up to about 45% compared to corn of the same genetic background but having a wild-type Bm gene.

Corn inbreds and hybrids carrying bm alleles and displaying the bm phenotype may be produced by corn breeding methods known in the art. In one embodiment, a corn inbred line is converted to the bm phenotype in a breeding program initiated from the $F_1$ progeny of a cross between a plant of a first inbred (wild-type for the bm phenotype) and plants of a second line carrying the desired bm allele. $F_1$ plants are backcrossed to the first inbred line until an inbred line is obtained that has substantially the same genotype as the original inbred line except for the replacement of the wild-type Bm gene by the mutant bm gene.

In another embodiment, a pedigree breeding program may be used in which two inbreds, one of which carries the bm phenotype, are crossed and new, unique inbreds are selected that carry desired yield and agronomic performance characteristics as well as the bm phenotype. Conversion programs, pedigree breeding programs, breeding programs using synthetics and other methods for obtaining bm inbreds are known in the art. See, e.g., Hallauer, et al. in Corn and Corn Improvement, Sprague et al., eds. pp. 463–564 (1988).

In addition to selecting and identifying plants containing a mutant bm gene, it is desirable to select concomitantly for plants having superior agronomic and yield performance characteristics.

Techniques for identifying plants displaying the brown midrib phenotype are known in the art. For example, the underside of leaves may be examined at 10–14 days before tassel emergence (4–6 leaf stage, 2–3 ft. height) for the appearance of a golden-brown or reddish-brown color on the midrib. Plants may also be examined at maturity by removing a leaf sheath and examining the stalk. The stalk has a golden-brown or reddish-brown color if the brown midrib phenotype is expressed. Brown pigment is also present in the cob and in the roots. Because the bm phenotype is recessive, the presence of the bm gene in heterozygotes can be determined by performing a self and evaluating the selfed progeny for the expected 3:1 segregation ratio. Alternatively, marker-assisted breeding techniques may be used, e.g., restriction fragment length polymorphisms (RFLP), simple sequence repeats (SSR), microsatellite markers or PCR markers. Marker-assisted breeding techniques are useful, in that plants heterozygous for the bm allele can be identified without the necessity for evaluating phenotypic ratios in selfed progeny.

Once inbreds having the bm phenotype and desired performance characteristics have been identified, each inbred is evaluated for the development of appropriate hybrid combinations by test crosses or top crosses to another inbred displaying the bm phenotype. Methods and tests for identifying appropriate hybrid combinations having the desired yield, maturity and other agronomic performance characteristics are known in the art.

Examples of corn inbreds suitable for producing corn silage include, without limitation, inbreds AR5252bm3, 7675bm3, 7677bm3, AR5251bm3 and AR5651bm3. Applicants have deposited seeds of the inbred lines indicated in Table 1 with the American Type Culture Collection (ATCC) Rockville, Md. 20852 U.S.A. The seeds deposited with the ATCC are taken from the same deposit maintained by Cargill, Inc., Wayzata, Minn., since prior to the filing date of this application. The deposits of the corn inbreds in Table 1 will be maintained without restriction in the ATCC depository for a period of 30 years, or 5 years after the most recent request, or for the effective life of the patent, whichever is longer, and will be replaced if the deposit becomes nonviable during that period.

TABLE 1

| Line Designation | ATCC Deposit No. | Date of Deposit |
| --- | --- | --- |
| AR5651bm3 | 203350 | October 9, 1998 |

Seeds possessing a mutant bm allele are also available from various universities and seed stock centers. These seeds can also be used to initiate a bm breeding program.

An inbred line according to the invention preferably is homozygous for a bm3 allele. Certain bm3 alleles have been sequenced, e.g., the bm3-1 and bm3-2 alleles. Vignols et al. Plant Cell 7:407–416 (1995). Alleles that have a deletion, e.g., a deletion similar to that in bm3-2, are preferred because such alleles are less likely to revert to wild-type.

It is known in the art that maize germplasm can be divided into a number of distinct heterotic groupings. Such groups include Reid Yellow Dent, Lancaster Sure Crop and subgroups such as Iowa Stiff Stalk Synthetic (Reid Yellow Dent) and Oh43 (Lancaster Sure Crop). One important aspect of a maize breeding program is the identification of the heterotic group to which a particular inbred belongs. By identifying the heterotic group or subgroup, it becomes possible to more clearly determine the appropriate types of crosses, in order to obtain sufficient levels of heterosis or hybrid vigor. Because of the large number of possible heterotic groupings to which a given inbred can belong, it is useful to ascertain which heterotic groups can be most advantageously used to form a hybrid combination from brown midrib inbreds. Inbreds having the mutant bm phenotype have not been tested in all possible heterotic groups for the effect of the bm phenotype on expression of the mutant trait and the effect on other agronomic traits.

Once a suitable pair of inbred lines has been identified and $F_1$ hybrid seed has been prepared therefrom, the resulting seed is planted and cultivated according to standard agronomic practices in the geographic area to which the hybrid is adapted. Growers will also typically take into account soil fertility, crop rotation practices and other factors specific to the locale in which the hybrid corn is being grown.

Typically, a substantially uniform assemblage of $F_1$ bm hybrid corn seeds is conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label indicates that the seeds therein are suitable for producing silage that can be fed to dairy cattle. Preferably, the package label indicates that the resulting silage is to be combined with a feed composition component as disclosed herein. The package label may also indicate that silage resulting from seeds contained therein may increase milk production when fed to lactating cows as disclosed herein.

$F_1$ hybrid corn plants derived from inbred lines of the invention may be grown to maturity and the seeds produced thereon harvested for use as grain. However, above-ground parts of the hybrid corn plants are preferably harvested after grain fill, but before drydown. Typically, the plants are harvested using a mechanical forage harvester which chops the above-ground portion of the plant into small pieces. Harvesting typically occurs when the color line is halfway down the kernel, based on the stage of seed maturity. The precise harvest time will depend, of course, upon geographical location and seasonal factors such as the weather. The chopped material is then ensiled by techniques known in the art, e.g., in trenches or in concrete stave silos. Microbial inoculants and/or preservatives may be added to promote silage formation, if desired.

Corn silage from bm hybrids is fed to dairy cattle as a total dairy cattle feed ration comprising bm silage and a feed composition. A feed composition component of the invention may be a complete feed form, a concentrate form, blender form or base mix form.

By complete feed form it is meant that the feed represents the cows entire grain ration. By concentrate form it is meant that the feed will be used as the primary supplemental protein source and would normally be fed with grain to meet the cows protein needs. By blender form it is meant that the feed will be mixed with approximately a 50:50 ratio with grain to form the complete grain ration. The base mix form is similar to the concentrate form, but is typically higher in protein content and is used at lower inclusion rates. The base mix form will be a primary, but often not the sole source of supplemental protein.

A complete feed form composition typically contains wheat middlings, corn, meat and bone meal, soybean meal, salt, macro-minerals, trace minerals and vitamins. Alternative or optional ingredients commonly include, but are not restricted to, fat, sunflower meal, feather meal, malt sprouts, distillers' grains, canola meal and soybean hulls. Other alternative or optional protein sources include, for example, blood meal, corn gluten meal, peanut meal, cottonseed meal, soybeans (extruded or roasted), wheat bran and high fat rice bran.

The nutrient composition of a complete feed composition component typically provides crude protein at from about 16% to about 27% on a dry matter basis, preferably about 22% to about 25%. Rumen undegraded protein (RUP) comprises from about 30% to about 50%, preferably from about 35% to about 45% of the total crude protein. The fat content is typically from about 4% to about 8%, preferably from about 4% to about 6%. Soluble protein (SP) typically comprises from about 15% to about 30% of the crude protein, preferably about 20% to about 25%. The NFC content typically comprises from about 36% to about 46% of the feed composition on a dry matter basis, preferably from about 39% to about 43%.

A concentrate form composition, a blender form composition or a base mix form composition can be prepared by those of skill in the art, based upon the complete feed composition discussed above.

In one embodiment, the complete feed form composition comprises about 7 to about 56 weight percent corn, about 20 to about 50 weight percent wheat middlings and about 0.25 to about 4 weight percent soybean meal. In a preferred embodiment, the complete feed form composition comprises about 35 weight percent corn, about 20 weight percent wheat middlings and about 2 weight percent soybean meal.

Grains fed with the blender, concentrate and base mix forms of the composition can include, but are not limited to, corn, barley, oats, millet, rice, sorghum and wheat. Intake of the total grain ration will typically range from 6 to about 37 pounds per day. If the composition is in the complete feed form, the percent protein level is preferably from about 14 to about 24 percent by weight. If the composition is in a form of a concentrate, the protein level is preferably from about 32 to about 48 percent by weight. If the composition is in the form of a blender, the protein level in the composition is from about 24 to about 26 percent by weight. If the composition is in the form of a base mix, the protein level is preferably from about 55 to about 65 percent by weight.

The silage component and the feed composition component are combined and fed to dairy cattle. The bm silage may comprise from about 5% by weight of the total dairy cattle feed ration to about 60% by weight of the total ration on a dry matter basis. The bm silage component of the ration preferably is about 20% to about 50% on a dry matter basis of the ration, more preferably from about 25% to about 35% by weight. Other roughage sources that may be used to complete the ration include, but are not limited to, corn silage from non-Bm corn plants, alfalfa haylage, grass silages (e.g., sudangrass, orchardgrass or sorghum-based silage), grass hays (e.g., sudangrass or orchardgrass) and alfalfa or clover hay, as is known in the art.

A dairy cattle feed ration according to the invention may be fed to both primiparous and multiparous cows, either in early, mid or late lactation.

A dairy cattle feed ration comprising bm corn silage provides significant increases in milk production compared to other dairy cattle feed rations. A dairy cattle feed ration formed by combining a silage component disclosed herein and a feed composition component leads to an increase in milk production of about 4 lbs/cow/day, preferably greater than about 5 lbs/cow/day, more preferably greater than about 8 lbs/cow/day. A dairy cattle feed ration as disclosed herein provides significant utility to the producer because of such increases in milk production.

The invention will be further understood with reference to the following illustrative embodiments, which are purely exemplary and should not be taken as limiting the true scope of the present invention as described in the claims.

EXAMPLE 1

Preparation of Silage from a Brown Midrib Hybrid

Inbred lines AR5252bm3 and 7675bm3 are crossed (AR5252bm3×7675bm3) to make $F_1$ hybrid seed carrying the brown midrib genotype. Control hybrid seed is prepared by crossing the unconverted parental lines, MED947×7675, respectively.

The control and bm hybrid seed is planted at a density of 24,900 kernels per acre and cultivated using a standard fertilization program. The corn is harvested 4 months after planting, using a forage harvester having a ⅜ in. theoretical length of cut (TLC) and a screen. The harvested material is placed in polyethylene bags (Ag Bags). If desired, the harvested material is treated with inoculant and/or preservative. The forage yield for bm corn silage is about 1 wet ton per acre less than the control hybrid corn.

Samples are collected from the polyethylene bags after 30 days of fermentation/storage and assayed for nutrient concentrations. Typical results are shown in Table 2. The control corn silage and the BMR corn silage are similar in nutrient composition, except for fiber digestibility and $NE_L$ concentration. The greater $NE_L$ concentration is likely related to the in vitro digestibility of NDF, ADF, and hemicellulose.

TABLE 2

Nutrient composition of corn silages[1]

| Nutrient | Control | BMR |
|---|---|---|
| Dry matter, % | 34.6 | 31.9 |
| Crude protein, % | 8.18 | 8.58 |
| Fat, % | 2.74 | 2.59 |
| ADF, % | 18.76 | 19.93 |
| NDF, % | 38.20 | 40.67 |
| Hemicellulose, % | 19.44 | 20.74 |
| NDF dig., % | 52.4 | 65.3 |
| ADF dig., % | 43.5 | 60.9 |
| Hemicellulose dig., % | 60.9 | 69.5 |
| Ash, % | 3.34 | 3.63 |
| NFC, % | 47.54 | 44.53 |
| $NE_L$, Mcal/cwt. | 76.0 | 80.5 |
| Ca, % | .19 | .19 |
| P, % | .23 | .22 |
| Mg, % | .14 | .13 |
| K, % | 1.09 | 1.27 |
| Na, % | .01 | .09 |
| Salt, % | .22 | .131 |

[1]Nutrients are expressed on a dry matter basis.

EXAMPLE 2

Formulation of a Dairy Cattle Feed Ration

The following experimental diets are developed to be fed as a total mixed ration (TMR). The following assumptions are used in ration formulation: the early lactation experimental dairy cow is estimated to weigh 1,400 lbs. and to produce 110 lbs. of milk with 3.30% fat, 3.10% milk protein and no body weight change. Dry matter intake (DMI) is predicted to be slightly less than 4.0% of body weight. The TMR is formulated to contain on a dry matter basis: 50% complete feed mix, 33% corn silage and 17% alfalfa haylage. The ingredient composition of the complete feed is given in Table 3 and the nutrient composition of the complete feed mix is given in Table 4.

TABLE 3

Ingredient Composition of Complete Feed[1]

| INGREDIENT | Composition (% by weight) |
|---|---|
| Corn, coarse ground | 38.7 |
| Wheat Middlings | 20.0 |
| Meat & Bone Meal (50% protein) | 1.5 |
| Hi Pro Soybean Meal (49% crude protein) | 1.9 |
| Feather Meal | 3.5 |
| Canola Meal | 20.0 |
| Animal fat | 2.3 |
| Minerals and Vitamins | 4.7 |
| Distillers grains | 7.4 |
| Total | 100.0 |

[1]As fed basis.

TABLE 4

Nutrient Composition of Complete Feed

| NUTRIENT | COMPOSITION[1] |
|---|---|
| Dry Matter | 88.0 |
| Crude Protein (CP) | 23.0 |
| Soluble Protein (SP as % of CP) | 21.0 |
| RUP (% of CP) | 45.0 |
| Fat | 5.0 |
| Net Energy of Lactation ($NE_L$) Meal/kg | 92.0 |
| Acid Detergent Fiber (ADF) | 9.3 |
| Neutral Detergent Fiber (NDF) | 19.5 |
| Non-Fiber Carbohydrate (NFC) | 43.0 |
| Calcium | 1.40 |
| Phosphorus | .90 |
| Magnesium | .45 |
| Sulfur | .50 |
| Salt | 1.50 |

[1]Percentages for nutrients given as % by weight on a dry matter basis

Brown midrib (BMR) or control corn silage (Example 2) are combined with complete feed mix and alfalfa haylage to form the rations, using each silage in an equal amount on a dry matter basis. Rations contain approximately 18.5% crude protein, 32% soluble protein and 40% rumen undegraded protein. Both rations are adjusted to a calculated pH of about 6.2. Both rations are balanced to meet or exceed mineral, vitamin and total bypass protein requirements.

EXAMPLE 3

Milk Production Using BMR Silage in a Dairy Cattle Ration 20 lactating dairy cows are utilized in a randomized complete block design experiment, consisting of 5 primiparous cows and 5 multiparous cows fed control silage and 5 primiparous cows and 5 multiparous cows fed BMR silage. Cows are randomly assigned after calving. During the fifth week postpartum, the cows are abruptly switched to the appropriate feeding ration and continued on that ration from week 5 to week 17 postpartum. Primiparous cows are producing more than 55 lbs./day of milk during the 4th week postpartum. Multiparous cows are producing greater than 65 lbs./day of milk during the 4th week postpartum. All cows are disease free and otherwise healthy. Cows are fed ad libitum for the duration of the experiment, twice daily at 12 hour intervals, if possible. Cows are fed to allow for 5 to 10% feed refusal.

The dietary ration and percentages of complete feed mix, corn silage and alfalfa haylage on a dry matter basis are given in Table 5.

TABLE 5

Dietary feeding guidelines to feed concentrate mix and forages

| Ration Content | Control ration % of DM | BMR ration % of DM | DM, % | Control ration % as Fed | BMR ration % as Fed |
|---|---|---|---|---|---|
| Control silage | 33.0 | — | 34.6 | 50.3 | — |
| BMR silage | — | 33.0 | 31.9 | — | 52.4 |
| Complete Feed | 50.9 | 50.0 | 88.0 | 30.0 | 28.8 |

TABLE 5-continued

Dietary feeding guidelines to feed concentrate mix and forages

| Ration Content | Control ration % of DM | BMR ration % of DM | DM, % | Control ration % as Fed | BMR ration % as Fed |
|---|---|---|---|---|---|
| Alfalfa Haylage | 17.0 | 17.0 | 45.6 | 19.7 | 18.9 |
| Total | 100.0 | 100.0 | | 100.0 | 100.0 |

Milk production is measured at each milking and reported daily. Two samples of milk are taken weekly from each cow for composition analysis, including fat, protein, lactose, solids-not-fat and somatic cell counts. Body weights are recorded weekly after calving. Body condition scores are recorded at approximately weeks 4, 8, 12 and 16 postpartum. The same employee records condition scores at each measurement time. Body conditions scores are recorded according to the definitions indicated in Table 6.

TABLE 6

Instructions for Body Condition Scoring

| Score | Definition |
|---|---|
| 1 | Loin area has limited flesh covering, is prominent and the ends of spinous processes are sharp to touch. Definite overhanging shelf effect is visible. Individual vertebrae of the hind quarters are prominent and distinct. Hooks and pin bones are notable. The area below the tail-head and between pin bones is severely depressed causing the bone structure of the area to appear extremely sharp. |
| 2 | Individual spinous processes are usually discernible but are not prominent. Ends of processes are sharp to touch, although they have greater flesh covering. The processes do not have a distinct overhanging shelf effect. Individual vertebrae of the hind quarters are not visually distinct but are readily distinguishable by palpitation. Hooks and pin bones are prominent, but the depression between them is less severe. The area below the tail-head and between the pin bones is depressed, but the bone structure is not devoid of flesh covering. |
| 3 | Spinous processes are discernible by applying slight pressure. Area over processes appears smooth and the overhanging shelf effect is not noticeable. Vertebrae of the hindquarters appear as a rounded ridge. Hooks and pin bones are rounded and smooth. The area between the pin bones and around the tail-head appear smooth without sign of fat deposition. |
| 4 | Individual spinous processes can be distinguished only by firm palpitation. Processes appear flat or rounded with no overhanging shelf effect. The ridge formed by the vertebrae of the hindquarters is rounded and smooth, flattening out as you move forward. Hooks are rounded, and the span between hooks is flat. The area around the tail-head and pin bones is rounded with evidence of fat deposition. |
| 5 | Bone structure of the vertebral column, spinous processes, hooks and pin bone regions is not visually apparent. Evidence of fat deposition is prominent. The tail head appears to be buried in fatty tissue. |

The results indicate that cows fed BMR silage have a statistically significant increase in milk production when comparing unadjusted means or when comparing covariate adjusted means. The increase is from about 4 lbs. milk/cow/day to about 11 lbs. milk/cow/day.

EXAMPLE 4

Development of Corn Inbred Lines and Hybrids Having a Brown Midrib Phenotype

Line MED947 is a corn inbred that has the characteristics shown in Table 7. Line MED947 was crossed to B73bm3 (stock no. 980392, obtained from the Department of Agronomy, Purdue University, West Lafayette, Ind.). After completing a conversion program, an inbred line designated as AR5252bm3 was obtained. The backcrossing program is shown in Table 8.

Line MED154 is a corn inbred that has the characteristics shown in Table 9. Line MED154 was backcrossed to AR5151bm3 as indicated in Table 10 to obtain line AR5251bm3. The bm3 allele in AR5151bm3 was obtained from A632bm3 (Purdue University).

Line MED058 is a corn inbred that has the characteristics shown in Table 11. Line MED058 was backcrossed with line AR5654bm3. The bm3 allele in AR5654bm3 was derived from Mo17bm3 (Purdue University).

Line 7675 was crossed to Oh545bm3 (stock no. 980390, Department of Agronomy, Purdue University) in a conversion program as shown in Table 8, resulting in an inbred line designated 7675bm3.

Line 7677 was crossed to Mo17bm3 (stock no. 980394, Department of Agronomy, Purdue University) in a conversion program as shown in Table 8, resulting in an inbred line designated as 7677bm3.

Characteristics of the inbred lines AR5252bm3, 7675bm3 and 7677bm3 are shown in Table 12. Data on flowering for six inbred lines is shown in Table 13.

Line AR5252bm3 was crossed as a female to 7675bm3 and to 7677bm3 to form $F_1$ hybrids XB657 and XB757, respectively. Characteristics of XB657 are shown in Table 14. Characteristics of XB757 are shown in Table 15.

Hybrid checks were prepared from crosses of AR5252×7675 and AR5252×7677. These $F_1$ hybrids do not exhibit the brown midrib phenotype.

Pairwise comparisons of forage yield, quality profiles and energy values for XB657 and unconverted control hybrid 657 are shown in Table 16. The same comparisons are shown for XB757 and control hybrid 757 in Table 17.

Lines AR5751bm3, AR5654bm3, AR5253bm3, A:R5153bm3 and AR5551bm3 were developed by backcrossing programs similar to those described above. Each of these lines exhibits the brown midrib phenotype. Characteristics of these lines are shown in Tables 18–23.

To the extent not already indicated, it will be understood by those of ordinary skill in the art: that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

TABLE 7

Description of Line MED947

COTYLEDON LEAF

| | |
|---|---|
| ANTHOCYANIN | N/A |
| LENGTH | N/A |

PLANT AND STALK

| | |
|---|---|
| PLANT HEIGHT | 7.50 ft. |
| EAR HEIGHT | 3.00 ft. |
| UNIFORMITY RATING | 8 |
| ANTHOCY. IN BRACE ROOTS | PRESENT |
| ANTHOCY. IN NODES | ABSENT |
| DIAM. AT 2nd NODE | 0.00 in. |
| ROOT RATING | N/A |

LEAVES

| | |
|---|---|
| ANGLE | UPRIGHT |
| COLOR | MEDIUM GREEN |
| TOTAL NUMBER | |
| NUMBER ABOVE EAR | 5–6 |
| LENGTH, EAR LEAF | 0 in. |
| MAX., WIDTH, EAR LEAF | 0.00 |
| ANTHOCYANIN, MARGIN | ABSENT |
| ANTHOCYANIN, SHEATH | ABSENT |
| PUBESCENCE, SHEATH | PRESENT |
| PUBESCENCE, MARGINS | PRESENT |
| PLANT, TILLERING TASSEL | 0.00 |

TASSEL

| | |
|---|---|
| COMPACTNESS | COMPACT |
| BRANCH ANGLE | <30 |
| NUMBER PRIMARY BRANCHES | 4–8 |
| SECONDARY BRANCH | PRESENT |
| LENGTH | N/A |
| SIZE RATING | 7 |
| TASSEL EXTENSION | PARTIALLY ENCLOSED |
| SHED IN BOOT? | NO |
| DIFFICULTY IN PULLING | AVERAGE |
| NUMBER LEAVES PULLED | 0 |
| ANTHER COLOR | YELLOW |
| GLUME COLOR - TIP | RED |
| - BASE | LIGHT GREEN |
| - BAND | RED |
| POLLEN SHED DURATION | AVERAGE |
| POLLEN AMOUNT RATING | AVERAGE |

EAR CHARACTERISTICS

| | |
|---|---|
| SILK COLOR | YELLOW |
| EAR LEAVES | ABSENT |

HUSK

| | |
|---|---|
| COVERAGE | COVERS TIP |
| LOOSENESS | TIGHT |
| EAR ANGLE RATING | 6 |
| SHANK LENGTH | <4 in. |
| EAR LENGTH | 6–9 in. |
| EAR SHAPE | CYLINDRICAL |
| UNIFORMITY | 8 |

KERNEL

| | |
|---|---|
| NO. ROWS | 16 |
| TYPE | SEMI DENT |
| SIZE | AVERAGE |
| BODY COLOR | YELLOW |
| CROWN COLOR | LIGHT YELLOW |

COB

| | |
|---|---|
| COLOR | PINK |
| DIAMETER MIDPOINT | <1 in. |

INSECT RESISTANCE

| | |
|---|---|
| ATTRACTIVE TO APHIDS | N/A |

DISEASE RESISTANCE RATINGS

| | |
|---|---|
| NORTHERN LEAF BLIGHT (R2) | 5B |
| SOUTHERN LEAF BLIGHT (R0) | 6B |
| NORTHERN COB LEAF SPOT (R3) | 6B |
| STEWARTS BACTERIAL WILT | 6B |

TABLE 7-continued

Description of Line MED947

| | |
|---|---|
| GREY LEAF SPOT | 8B |
| EYESPOT | 6B |
| ANTHRACNOSE | 6B |

(9 = Resistant, 1 = Susceptible)
(Letter indicates confidence level)

TABLE 8

Inbred Line Conversion to Brown MidRib

AR5252bm3

| | |
|---|---|
| (MED947XB73bm$_3$) | MED947BC$_6$ |
| (MED947XB73bm$_3$) | MED947BC$_5$S$_1$ |
| (MED947XB73bm$_3$) | MED947BC$_5$ |
| (MED947XB73bm$_3$) | MED947BC$_4$ |
| (MED947XB73bm$_3$) | MED947BC$_3$S$_1$ |
| (MED947XB73bm$_3$) | MED947BC$_3$ |
| (MED947XB73bm$_3$) | MED947BC$_2$ |
| (MED947XB73bm$_3$) | MED947BC$_1$S$_1$ |
| (MED947XB73bm$_3$) | MED947BC$_1$ |
| (MED947XB73bm$_3$) | F$_1$ |
| (MED947XB73bm$_3$) | F$_0$ |

7675bm3

| | |
|---|---|
| (7675xOh545bm$_3$) | 7675BC$_6$S$_1$ |
| (7675xOh545bm$_3$) | 7675BC$_6$ |
| (7675xOh545bm$_3$) | 7675BC$_5$ |
| (7675xOh545bm$_3$) | 7675BC$_4$ |
| (7675xOh545bm$_3$) | 7675BC$_3$S$_1$ |
| (7675xOh545bm$_3$) | 7675BC$_3$ |
| (7675xOh545bm$_3$) | 7675BC$_2$ |
| (7675xOh545bm$_3$) | 7675BC$_1$S$_1$ |
| (7675xOh545bm$_3$) | 7675BC$_1$ |
| (7675xOh545bm$_3$) | 7675F$_1$ |
| (7675xOh545bm$_3$) | F$_0$ |

7677bm3

| | |
|---|---|
| (7677xMo17bm$_3$) | 7677BC$_5$S$_1$ |
| (7677xMo17bm$_3$) | 7677BC$_5$ |
| (7677xMo17bm$_3$) | 7677BC$_4$ |
| (7677xMo17bm$_3$) | 7677BC$_3$S$_1$ |
| (7677xMo17bm$_3$) | 7677BC$_3$ |
| (7677xMo17bm$_3$) | 7677BC$_2$ |
| (7677XMo17bm$_3$) | 7677BC$_1$S$_1$ |
| (7677XMo17bm$_3$) | 7677BC$_1$ |
| (7677xMo17bm$_3$) | F$_1$ |
| (7677xMo17bm$_3$) | F$_0$ |

TABLE 9

Description of Line MED154

COTYLEDON LEAF

| | |
|---|---|
| ANTHOCYANIN | N/A |
| LENGTH | <2 |

PLANT AND STALK

| | |
|---|---|
| PLANT HEIGHT | 7.0 ft. |
| EAR HEIGHT | 2.0 ft. |
| UNIFORMITY RATING | 7 |
| ANTHOCY. IN BRACE ROOTS | PRESENT |
| ANTHOCY. IN NODES | ABSENT |
| DIAM. AT 2nd NODE | 1.0 in. |
| ROOT RATING | AVERAGE |

LEAVES

| | |
|---|---|
| ANGLE | VERY |
| COLOR | MEDIUM |
| TOTAL NUMBER | 10–15 |
| NUMBER ABOVE EAR | 5–6 |

TABLE 9-continued

Description of Line MED154

| | |
|---|---|
| LENGTH, EAR LEAF | 34 in. |
| MAX., WIDTH, EAR LEAF | 4.50 |
| ANTHOCYANIN, MARGIN | PRESENT |
| ANTHOCYANIN, SHEATH | ABSENT |
| PUBESCENCE, SHEATH | ABSENT |
| PUBESCENCE, MARGINS | PRESENT |
| PLANT, TILLERING TASSEL | 0.00 |
| TASSEL | |
| COMPACTNESS | AVERAGE |
| BRANCH ANGLE | 30–60 |
| NUMBER PRIMARY BRANCHES | <4 |
| SECONDARY BRANCH | ABSENT |
| LENGTH | 10–14 |
| SIZE RATING | 2 |
| TASSEL EXTENSION | PARTIALLY ENCLOSED |
| TASSEL FERTILITY | 0 |
| SHED IN BOOT? | NO |
| DIFFICULTY IN PULLING | AVERAGE |
| NUMBER LEAVES PULLED | 1 |
| ANTHER COLOR | PINK |
| GLUME COLOR - TIP | LIGHT GREEN |
| - BASE | RED |
| - BAND | DARK GREEN |
| POLLEN SHED DURATION | SHORT |
| POLLEN AMOUNT RATING | LONG |
| EAR CHARACTERISTICS | |
| SILK COLOR | RED |
| EAR LEAVES | MEDIUM |
| HUSK | |
| COVERAGE | COVERS TIP |
| LOOSENESS | LOOSE |
| EAR ANGLE RATING | 6 |
| SHANK LENGTH | 4–12 |
| EAR LENGTH | 6–9 |
| EAR SHAPE | CONICAL |
| UNIFORMITY | 7 |
| KERNEL | |
| NO. ROWS | 16 |
| TYPE | DENT |
| SIZE | AVERAGE |
| BODY COLOR | ORANGE |
| CROWN COLOR | YELLOW |
| COB | |
| COLOR | WHITE |
| DIAMETER MIDPOINT | 1–2 |
| INSECT RESISTANCE | |
| ATTRACTIVE TO APHIDS | YES |

TABLE 10

Inbred Line Conversion to Brown Midrib

AR5251bm3

(MED154XAR5151bm$_3$) C$_5$
(MED154XAR5151bm$_3$) C$_4$
(MED154XAR5151bm$_3$) C$_3$S$_1$
(MED154XAR5151bm$_3$) C$_3$
(MED154XAR5151bm$_3$) C$_2$
(MED154XAR5151bm$_3$) C$_1$S$_1$
(MED154XAR5151bm$_3$) C$_1$
(MED154XAR5151bm$_3$) F$_1$
(MED154XAR5151bm$_3$) F$_0$
AR5651bm3

(MED058XAR5654bm$_3$) C$_5$S$_1$
(MED058XAR5654bm$_3$) C$_5$
(MED058XAR5654bm$_3$) C$_4$

TABLE 10-continued

Inbred Line Conversion to Brown Midrib (MED058XAR56S4bm$_3$) C$_3$
(MED058XAR56S4bm$_3$) C$_2$
(MED058XAR5654bm$_3$) C$_1$S$_1$
(MED058XAR5654bm$_3$) C$_1$
(MED058XAR5654bm$_3$) F$_1$
(MED058XAR5654bm$_3$) F$_0$

TABLE 11

Description of Line MED058

| | |
|---|---|
| COTYLEDON LEAF | |
| ANTHOCYANIN | N/A |
| LENGTH | <2 |
| PLANT AND STALK | |
| PLANT HEIGHT | 6.5 ft. |
| EAR HEIGHT | 3.0 ft. |
| UNIFORMITY RATING | 7 |
| ANTHOCY. IN BRACE ROOTS | PRESENT |
| ANTHOCY. IN NODES | ABSENT |
| DIAM. AT 2nd NODE | 1.0 in. |
| ROOT RATING | AVERAGE |
| LEAVES | |
| ANGLE | UPRIGHT |
| COLOR | LIGHT GREEN |
| TOTAL NUMBER | 10–15 |
| NUMBER ABOVE EAR | >6 |
| LENGTH, EAR LEAF | 21 in. |
| MAX., WIDTH, EAR LEAF | 3.00 |
| ANTHOCYANIN, MARGIN | PRESENT |
| ANTHOCYANIN, SHEATH | ABSENT |
| PUBESCENCE, SHEATH | ABSENT |
| PUBESCENCE, MARGINS | ABSENT |
| PLANT, TILLERING TASSEL | 0.00 |
| TASSEL | |
| COMPACTNESS | LOOSE |
| BRANCH ANGLE | >60 |
| NUMBER PRIMARY BRANCHES | 4–6 |
| SECONDARY BRANCH | ABSENT |
| LENGTH | >14 |
| SIZE RATING | 5 |
| TASSEL EXTENSION | PARTIALLY ENCLOSED |
| TASSEL FERTILITY | 0 |
| SHED IN BOOT? | NO |
| DIFFICULTY IN PULLING | EASY |
| NUMBER LEAVES PULLED | 2 |
| ANTHER COLOR | YELLOW |
| GLUME COLOR - TIP | LIGHT GREEN |
| - BASE | LIGHT GREEN |
| - BAND | DARK GREEN |
| POLLEN SHED DURATION | AVERAGE |
| POLLEN AMOUNT RATING | LIGHT |
| EAR CHARACTERISTICS | |
| SILK COLOR | YELLOW |
| EAR LEAVES | ABSENT |
| HUSK | |
| COVERAGE | COVERS TIP |
| LOOSENESS | AVERAGE |
| EAR ANGLE RATING | 5 |
| SHANK LENGTH | <4 |
| EAR LENGTH | 6–9 |
| EAR SHAPE | CYLINDRICAL |
| UNIFORMITY | 9 |
| KERNEL | |
| NO. ROWS | 12 |
| TYPE | DENT |
| SIZE | AVERAGE |

TABLE 11-continued

Description of Line MED058

| | |
|---|---|
| BODY COLOR | ORANGE |
| CROWN COLOR | YELLOW |
| COB | |
| | |
| COLOR | WHITE |
| DIAMETER MIDPOINT | <1 |
| INSECT RESISTANCE | |
| | |
| ATTRACTIVE TO APHIDS | NO |

TABLE 12

Description of Line 7675bm3

7675bm3

COTYLEDON LEAF

| | |
|---|---|
| ANTHOCYANIN | PRESENT |
| LENGTH | 2–3 |
| PLANT AND STALK | |
| | |
| PLANT HEIGHT | 5.5 ft. |
| EAR HEIGHT | 3.0 ft. |
| UNIFORMITY RATING | 2 |
| ANTHOCY. IN BRACE ROOTS | PRESENT |
| ANTHOCY. IN NODES | ABSENT |
| DIAM. AT 2nd NODE | 1.1 in. |
| ROOT RATING | EXCELLENT |
| LEAVES | |
| | |
| ANGLE | UPRIGHT |
| COLOR | VARIGATED |
| TOTAL NUMBER | 10–15 |
| NUMBER ABOVE EAR | 5–6 |
| LENGTH, EAR LEAF | 26 in. |
| MAX., WIDTH, EAR LEAF | 3.50 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | ABSENT |
| PLANT, TILLERING TASSEL | 0.00 |
| TASSEL | |
| | |
| COMPACTNESS | AVERAGE |
| BRANCH ANGLE | 30–60 |
| NUMBER PRIMARY BRANCHES | 4–8 |
| SECONDARY BRANCH | ABSENT |
| LENGTH | 10–14 in. |
| TASSEL FERTILITY | 1 |
| SIZE RATING | 6 |
| TASSEL EXTENSION | PARTIALLY ENCLOSED |
| SHED IN BOOT? | NO |
| DIFFICULTY IN PULLING | AVERAGE |
| NUMBER LEAVES PULLED | 1 |
| ANTHER COLOR | YELLOW |
| GLUME COLOR - TIP | LIGHT GREEN |
| - BASE | YELLOW |
| - BAND | DARK GREEN |
| POLLEN SHED DURATION | SHORT |
| POLLEN AMOUNT RATING | HEAVY |
| EAR CHARACTERISTICS | |
| | |
| SILK COLOR | YELLOW |
| EAR LEAVES | ABSENT |
| HUSK | |
| | |
| COVERAGE | SHORT |
| LOOSENESS | N/A |
| EAR ANGLE RATING | 8 |
| SHANK LENGTH | 4–12 |
| EAR LENGTH | 6–9 |
| EAR SHAPE | CYLINDRICAL |
| UNIFORMITY | 7 |

TABLE 12-continued

KERNEL

| | |
|---|---|
| NO. ROWS | 8–10 |
| TYPE | SEMI DENT |
| SIZE | AVERAGE |
| BODY COLOR | ORANGE |
| CROWN COLOR | YELLOW |
| COB | |
| | |
| COLOR | WHITE |
| DIAMETER MIDPOINT | <1 |
| INSECT RESISTANCE | |
| | |
| ATTRACTIVE TO APHIDS | NO |

7677bm3

COTYLEDON LEAF

| | |
|---|---|
| ANTHOCYANIN | PRESENT |
| LENGTH | 2–3 |
| PLANT AND STALK | |
| | |
| PLANT HEIGHT | 5.5 ft. |
| EAR HEIGHT | 1.0 ft. |
| UNIFORMITY RATING | 8 |
| ANTHOCY. IN BRACE ROOTS | PRESENT |
| ANTHOCY. IN NODES | ABSENT |
| DIAM. AT 2nd NODE | 1.1 in. |
| ROOT RATING | EXCELLENT |
| LEAVES | |
| | |
| ANGLE | DROOPING |
| COLOR | LIGHT GREEN |
| TOTAL NUMBER | 10–15 |
| NUMBER ABOVE EAR | 5–6 |
| LENGTH, EAR LEAF | 31 in. |
| MAX., WIDTH, EAR LEAF | 3.00 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | PRESENT |
| PLANT, TILLERING TASSEL | 0.00 |
| TASSEL | |
| | |
| COMPACTNESS | AVERAGE |
| BRANCH ANGLE | 30–60 |
| NUMBER PRIMARY BRANCHES | 4–8 |
| SECONDARY BRANCH | ABSENT |
| LENGTH | >14 in. |
| TASSEL FERTILITY | 5 |
| SIZE RATING | 7 |
| TASSEL EXTENSION | PARTIALLY ENCLOSED |
| SHED IN BOOT? | NO |
| DIFFICULTY IN PULLING | EASY |
| NUMBER LEAVES PULLED | 1 |
| ANTHER COLOR | YELLOW |
| GLUME COLOR - TIP | RED |
| - BASE | RED |
| - BAND | DARK GREEN |
| POLLEN SHED DURATION | N/A |
| POLLEN AMOUNT RATING | LONG |
| EAR CHARACTERISTICS | |
| | |
| SILK COLOR | YELLOW |
| EAR LEAVES | ABSENT |
| HUSK | |
| | |
| COVERAGE | LONG |
| LOOSENESS | N/A |
| EAR ANGLE RATING | 6 |
| SHANK LENGTH | <4 |
| EAR LENGTH | 6–9 |
| EAR SHAPE | CYLINDRICAL |
| UNIFORMITY | 7 |
| KERNEL | |
| | |
| NO. ROWS | 12 |
| TYPE | SEMI DENT |
| SIZE | AVERAGE |

TABLE 12-continued

| | |
|---|---|
| BODY COLOR | ORANGE |
| CROWN COLOR | YELLOW |
| COB | |
| COLOR | PINK |
| DIAMETER MIDPOINT | 1–2 |
| INSECT RESISTANCE | |
| ATTRACTIVE TO APHIDS | NO |
| AR5252bm3 | |
| COTYLEDON LEAF | |
| ANTHOCYANIN | PRESENT |
| LENGTH | 2–3 |
| PLANT AND STALK | |
| PLANT HEIGHT | 6.0 ft. |
| EAR HEIGHT | 2.0 ft. |
| UNIFORMITY RATING | 4 |
| ANTHOCY. IN BRACE ROOTS | PRESENT |
| ANTHOCY. IN NODES | ABSENT |
| DIAM. AT 2nd NODE | 1.1 in. |
| ROOT RATING | EXCELLENT |
| LEAVES | |
| ANGLE | UPRIGHT |
| COLOR | MEDIUM GREEN |
| TOTAL NUMBER | 10–15 |
| NUMBER ABOVE EAR | 5–6 |
| LENGTH, EAR LEAF | 30 in. |
| MAX., WIDTH, EAR LEAF | 4.00 |
| ANTHOCYANIN, MARGIN | ABSENT |
| ANTHOCYANIN, SHEATH | PRESENT |
| PUBESCENCE, SHEATH | ABSENT |
| PUBESCENCE, MARGINS | ABSENT |
| PLANT, TILLERING TASSEL | 0.00 |
| TASSEL | |
| COMPACTNESS | COMPACT |
| BRANCH ANGLE | <30 |
| NUMBER PRIMARY BRANCHES | 4–8 |
| SECONDARY BRANCH | PRESENT |
| LENGTH | >14 in. |
| TASSEL FERTILITY | 7 |
| SIZE RATING | 4 |
| TASSEL EXTENSION | PARTIALLY ENCLOSED |
| SHED IN BOOT? | NO |
| DIFFICULTY IN PULLING | EASY |
| NUMBER LEAVES PULLED | 1 |
| ANTHER COLOR | YELLOW |
| GLUME COLOR - TIP | RED |
| - BASE | YELLOW |
| - BAND | DARK GREEN |
| POLLEN SHED DURATION | SHORT |
| POLLEN AMOUNT RATING | LONG |
| EAR CHARACTERISTICS | |
| SILK COLOR | YELLOW |
| EAR LEAVES | ABSENT |
| HUSK | |
| COVERAGE | COVERS TIP |
| LOOSENESS | N/A |
| EAR ANGLE RATING | 6 |
| SHANK LENGTH | 4–12 |
| EAR LENGTH | 6–9 |
| EAR SHAPE | CYLINDRICAL |
| UNIFORMITY | 8 |
| KERNEL | |
| NO. ROWS | 16 |
| TYPE | DENT |
| SIZE | AVERAGE |
| BODY COLOR | ORANGE |
| CROWN COLOR | YELLOW |
| COB | |
| COLOR | PINK |

TABLE 12-continued

| | |
|---|---|
| DIAMETER MIDPOINT | 1–2 |
| INSECT RESISTANCE | |
| ATTRACTIVE TO APHIDS | NO |

Parental Description Legend

COTYLEDON LEAF

Anthocyanin (Present, Absent)
Length (<2, 2–3, >3 inches)
PLANT AND STALK

Plant Height (in feet)
Ear Height (in feet)
Uniformity (9–1 rating)
Anthocyanin In Brace Roots (Absent, Present, Dark)
Anthocyanin In Nodes (Ab, Present)
Stk Diameter at 2nd Node (in inches)
Root Rating (9 = Good Roots, 5 = Average Roots, 1 = Bad Roots)
LEAVES Angle (Very Erect, Upright, Horizontal, Drooping)
Color (Dark Green, Medium Green, Light Green, Variegated)
Total # (<9, 10–15, >15)
Above Ear (<5, 5–6, >6)
Length, Ear Leaf (in inches)
Max. Width, Ear Leaf (in inches)
Anthrocyanin, Margin (Absent, Present)
Anthrocyanin, Sheath (Absent, present)
Pubescence, Sheath (Absent, Present, Very Hairy)
Pubescence, Margins (Absent, Present)
Plants, Tillering Tassel (%) Percentage
TASSEL Compactness (Loose, Average, Compact)
Branch Angle (<30, 30–60, >60)
, Primary Branches (<4, 4–8, >8)
Secondary Branches (Absent, Present)
Length (<10 in., 10–14, >14 in.)
Size (9–1) Rating
Shed in Boot (Yes, No)
Tassel Extension (Enclosed, Partially Enclosed, Open)
Tassel Fertility (9 = Male Sterile, 7 = Male Sterile, Anthers Extruded and No Pollen, 5 = Intermediate With Some Viable and Nonviable Pollen, 3 = Near Normal Pollen, 1 = Completely Normal Pollen Shed and Viability)
Difficulty in Pulling (Easy, Average, Hard)
Leaves Pulled (Ave)
Anther Color (Yellow, Green, Pink, Red, Purple)
Glume Color Tip (Green, Light Green, Red, Yellow)
Base (Green, Light Green, Red, Yellow)
Banded (Dark Green, Red, Purple)
Pollen shed Duration (Short, Average, Long)
Pollen Amount (Low, Average, Heavy)
EAR CHARACTERISTICS Silk Color (Green, Yellow, Pink, Red, Purple)
Ear Leaves (Absent, Medium, Long)
Husk Coverage (Short, Covers tip, Long)
Looseness (Loose, Average, Tight)
Ear Angle at Harvest (9–1) Rating
Shank Length (<4, 4–12, >12)
Ear Length (<6, 6–9, >9)
Ear Shape (Cylindrical, Conical, Cylindrical/Conical)
Uniformity (9–1) Rating
Kernel No. Rows (8–10, 12, 14, 16, >18)
Type (Flint, Semi dent, Dent, Rough dent)
Size (Small, Average, Large)
Body Color (White, Light Yellow, Yellow, Orange, Red)

TABLE 12-continued

Crown Color (White, Light Yellow, Yellow, Orange, Red)
Cob

Color (Red, Pink, White)
Diameter Midpoint (<1, 1–2, >2)
INSECT RESISTANCE

Attractive to Aphids (Yes, Average, No)

TABLE 13

Flowering Characteristics of bm Inbred Lines

| 7675bm3 | | AR5252bm3 | | 7677bm3 | |
|---|---|---|---|---|---|
| Slk Heat 1: | 1,564 | Slk Heat 1: | 1,534 | Slk Heat 1: | 1,683 |
| Slk Heat M: | 1,587 | Slk Heat M: | 1,607 | Slk Heat M: | 1,738 |
| Slk Heat F: | 1,633 | Slk Heat F: | 1,587 | Slk Heat F: | 1,794 |
| Slk Days 1: | 86 | Slk Days 1: | 85 | Slk Days 1: | 91 |
| Slk Days M: | 87 | Slk Days M: | 88 | Slk Days M: | 93 |
| Slk Days F: | 89 | Slk Days F: | 87 | Slk Days F: | 95 |
| Pol Heat 1: | 1,534 | Pol Heat 1: | 1,505 | Pol Heat 1: | 1,419 |

TABLE 13-continued

Flowering Characteristics of bm Inbred Lines

| Pol Heat M: | 1,587 | Pol Heat M: | 1,534 | Pol Heat M: | 1,587 |
|---|---|---|---|---|---|
| Pol Heat F: | 1,607 | Pol Heat F: | 1,587 | Pol Heat F: | 1,633 |
| Pol Days 1: | 85 | Pol Days 1: | 84 | Pol Days 1: | 80 |
| Pol Days M: | 87 | Pol Days M: | 85 | Pol Days M: | 87 |
| Pol Days F: | 88 | Pol Days F: | 87 | Pol Days F: | 89 |

| AR5651bm3 | | AR5251bm3 | |
|---|---|---|---|
| Slk Heat 1: | 1,387 | Slk Heat 1: | 1,552 |
| Slk Heat M: | 1,437 | Slk Heat M: | 1,582 |
| Slk Heat F: | 1,479 | Slk Heat F: | 1,656 |
| Slk Days 1: | 83 | Slk Days 1: | 91 |
| Slk Days M: | 85 | Slk Days M: | 93 |
| Slk Days F: | 87 | Slk Days F: | 97 |
| Pol Heat 1: | 1,304 | Pol Heat 1: | 1,539 |
| Pol Heat M: | 1,387 | Pol Heat M: | 1,552 |
| Pol Heat F: | 1,459 | Pol Heat F: | 1,596 |
| Pol Days 1: | 79 | Pol Days 1: | 90 |
| Pol Days M: | 83 | Pol Days M: | 91 |
| Pol Days F: | 86 | Pol Days F: | 94 |

TABLE 14

Trait Summary for XB657

| Trait: | RATING | SCALE | DEFINITION |
|---|---|---|---|
| Yield for Maturity (9–1) | 9 | 9–1 | 9 = GOOD 1 = POOR |
| Stalk Strength (9–1) | Acceptable | 9–1 | 9 = GOOD 1 = POOR |
| Root Strength-Summer (9–1) | 9 | 9–1 | 9 = GOOD 1 = POOR |
| Root Strength-Fall (9–1) | NA | 9–1 | 9 = GOOD 1 = POOR |
| Testweight (9–1) | NA | 9–1 | 9 = GOOD 1 = POOR |
| Drydown (9–1) | NA | 9–1 | 9 = GOOD 1 = POOR |
| Ear Retention (9–1) | 9 | 9–1 | 9 = GOOD 1 = POOR |
| Early Vigor (9–1) | 5 | 9–1 | 9 = GOOD 1 = POOR |
| Seedling Purple Color (9–1) | 4 | 9–1 | 9 = NO PURPLE 1 = DARK PURPLE |
| Greensnap Potential (9–1) | 9 | 9–1 | 9 = LOW 1 = HIGH |
| Drought Stress (9–1) | 7 | 9–1 | 9 = GOOD 1 = POOR |
| Stay Green (9–1) | 8 | 9–1 | 9 = GOOD 1 = POOR |
| Plant Health (9–1) | 7 | 9–1 | 9 = GOOD 1 = POOR |
| Recommended Population (H M L) | H | H,M,L | HIGH, MEDIUM, LOW |
| Plant Height (S MS M MT T) | 8.0 | S,MS,M,MT,T | SHORT/MSHORT/MODERATE/MTALL/TA |
| Ear Height (S MS M MT T) | 3.5 | S,MS,M,MT,T | SHORT/MSHORT/MODERATE/MTALL/TA |
| Cargill RM (# Days) | 115 (NA) | DAYS | # DAYS |
| Flowering Date (E M L) | M | E,M,L | EARLY, MEDIUM, LATE |
| GDU's to Mid-Silk (#) | 1464 | # | # UNITS |
| GDU's to Black Layer (#) | 2694 | # | # UNITS |
| Plant Color (L M D) | M | L,M,D | LIGHT, MEDIUM, DARK |
| Leaf Angle (E U H D) | U | E,U,H,D | ERECT/UPRIGHT/HORIZONTAL/DROOPY |
| Leaf Width (W M N) | M | W,M,N | WIDE, MEDIUM, NARROW |
| Tillers (9–1) | 8 | 9–1 | 9 = NONE 1 = MANY |
| Shank Length (9–1) | 5 | 9–1 | 9 = SHORT 1 = LONG |
| Husk Coverage (9–1) | 8 | 9–1 | 9 = GOOD 1 = POOR |
| Ear Tip Fill (9–1) | 6 | 9–1 | 9 = GOOD 1 = POOR |
| Ear Length (L M S) | M | L,M,S | LONG, MEDIUM, SHORT |
| Ear Girth (G M S) | M | G,M,S | GIRTHY, MEDIUM, SLENDER |
| Ear Flex (9–1) | NA | 9–1 | 9 = GOOD 1 = POOR |
| Kernel Rows (# Range) | 14–16 | # | # RANGE |
| Kernel Depth (S M D) | D | S,M,D | SHALLOW, MODERATE, DEEP |
| Cob Color (R P W) | P | R,P,W | RED, PINK, WHITE |
| Kernel Color (W Y G B O R) | Y | W,Y,G,B,O,R | WHITE, YLLW, GLD, BRNZ, ORNG, RED |
| Kernel Texture (F SF SD D) | SD | F,SF,SD,D | FLINT, SEMIFLINT, SEMIDENT, DENT |

TABLE 15

Trait Summary for XB757

| Trait: | RATING | SCALE | DEFINITION |
|---|---|---|---|
| Yield for Maturity (9–1) | 7 | 9–1 | 9 = GOOD 1 = POOR |
| Stalk Strength (9–1) | Acceptable | 9–1 | 9 = GOOD 1 = POOR |
| Root Strength-Summer (9–1) | 9 | 9–1 | 9 = GOOD 1 = POOR |
| Root Strength - Fall (9–1) | NA | 9–1 | 9 = GOOD 1 = POOR |
| Testweight (9–1) | NA | 9–1 | 9 = GOOD 1 = POOR |
| Drydown (9–1) | NA | 9–1 | 9 = GOOD 1 = POOR |
| Ear Retention (9–1) | 9 | 9–1 | 9 = GOOD 1 = POOR |
| Eary Vigor (9–1) | 5 | 9–1 | 9 = GOOD 1 = POOR |
| Seedling Purple Color (9–1) | | 9–1 | 9 = NO PURPLE 1 = DARK PURPLE |
| Greensnap Potential (9–1) | 8 | 9–1 | 9 = LOW 1 = HIGH |
| Drought Stress (9–1) | 8 | 9–1 | 9 = GOOD 1 = POOR |
| Stay Green (9–1) | 8 | 9–1 | 9 = GOOD 1 = POOR |
| Plant Health (9–1) | 8 | 9–1 | 9 = GOOD 1 = POOR |
| Recommended Population (H M L) | H | H, M, L | HIGH, MEDIUM, LOW |
| Plant Height (S MS M MT T) | 8.5 | S, MS, M, MT, T | SHORT/MSHORT/MODERATE/MTALL/TA |
| Ear Height (S MS M MT T) | 3.0 | S, MS, M, MT, T | SHORT/MSHORT/MODERATE/MTALL/TA |
| Cargill RM (# Days) | | DAYS | # DAYS |
| Flowering Date (E M L) | M | E, M, L | EARLY, MEDIUM, LATE |
| GDU's to Mid-Silk (#) | 1529 | # | # UNITS |
| GDU's to Black Layer (#) | NA | # | # UNITS |
| Plant Color (L M D) | | L, M, D | LIGHT, MEDIUM, DARK |
| Leaf Angle (E U H D) | | E, U, H, D | ERECT/UPRIGHT/HORIZONTAL, DROOPY |
| Leaf Width (W M N) | | W, M, N | WIDE, MEDIUM, NARROW |
| Tillers (9–1) | | 9–1 | 9 = NONE 1 = MANY |
| Shank Length (9–1) | | 9–1 | 9 = SHORT 1 = LONG |
| Husk Coverage (9–1) | | 9–1 | 9 = GOOD 1 = POOR |
| Ear Tip Fill (9–1) | | 9–1 | 9 = GOOD 1 = POOR |
| Ear Length (L M S) | | L, M, S | LONG, MEDIUM, SHORT |
| Ear Girth (G M S) | | G, M, S | GIRTHY, MEDIUM, SLENDER |
| Ear Flex (9–1) | NA | 9–1 | 9 = GOOD 1 = POOR |
| Kernel Rows (# Range) | | # | # RANGE |
| Kernel Depth (S M D) | | S, M, D | SHALLOW, MODERATE, DEEP |
| Cob Color (R P W) | P | R, P, W | RED, PINK, WHITE |
| Kernel Color (W Y G B O R) | | W, Y, G, B, O, R | WHITE, YLLW, GLD, BRNZ, ORNG, RED |
| Kernel Texture (F SF SD D) | | F, SF, SD, D | FLINT, SEMI-FLINT, SEMI-DENT, DENT |

TABLE 16

Pairwise Comparison of XB657 and XB657*

| Traits | XB657 | XB657 | Range | # Loc. |
|---|---|---|---|---|
| Plant Features | | | | |
| Plant Hgt | 45.54 | 47.18 | −1.64 | 5 |
| Ear Hgt | 18.80 | 19.80 | −1.00 | 5 |
| Yield Profile | | | | |
| 70% Tons/A | 25.00 | 27.49 | −2.49 | 6 |
| DM Tons/A | 7.50 | 8.25 | −0.75 | 6 |
| DDM Tons/A | 5.90 | 6.07 | −0.17 | 6 |
| Quality Profile | | | | |
| % ADF | 23.18 | 24.83 | −1.65 | 6 |
| % NDF | 43.56 | 45.08 | −1.52 | 6 |
| % ASH | 4.62 | 4.51 | 0.11 | 6 |
| % CP | 8.92 | 8.29 | 0.63 | 6 |
| % IVTD | 78.75 | 73.26 | 5.49 | 6 |
| % IVCWD | 50.99 | 40.64 | 10.35 | 6 |
| % WP Mst | 70.83 | 66.54 | 4.29 | 6 |
| % WP DM | 29.17 | 33.46 | −4.29 | 6 |
| Energy Values | | | | |
| TDN | 67.97 | 66.28 | 1.69 | 6 |
| NEL (Mcal/LB) | 0.69 | 0.67 | 0.02 | 6 |
| NFC % | 39.80 | 39.02 | 0.78 | 6 |
| Lbs CP/A | 1,330.26 | 1,355.60 | −25.34 | 6 |
| Lbs TDN/A | 10,223.68 | 11,006.10 | −782.42 | 6 |
| Lbs NEL/A | 10,295.38 | 11,028.58 | −733.20 | 6 |
| Lbs DDM/Ton | 1,574.90 | 1,465.23 | 109.67 | 6 |
| LBS CP/Ton | 178.40 | 165.87 | 12.53 | 6 |

*Summary over two years

TABLE 17

Pairwise Comparison of XB757 and 757

| Traits | XB757 | 757 | Range | # Loc. |
|---|---|---|---|---|
| Plant Features | | | | |
| Plant Hgt | 45.28 | 49.38 | −4.10 | 5 |
| Ear Hgt | 19.06 | 21.42 | −2.36 | 5 |
| Yield Profile | | | | |
| 70% Tons/A | 27.00 | 30.23 | −3.23 | 6 |
| DM Tons/A | 8.10 | 9.07 | −0.97 | 6 |
| DDM Tons/A | 6.22 | 6.50 | −0.28 | 6 |
| Quality Profile | | | | |
| % ADF | 23.29 | 25.39 | −2.10 | 6 |
| % NDF | 44.96 | 46.97 | −2.01 | 6 |
| % ASH | 4.59 | 4.32 | 0.27 | 6 |
| % CP | 8.49 | 8.12 | 0.37 | 6 |
| % IVTD | 76.65 | 71.79 | 4.86 | 6 |
| % IVCWD | 47.88 | 39.89 | 7.99 | 6 |
| % WP Mst | 69.93 | 68.17 | 1.76 | 6 |
| % WP DM | 30.07 | 31.83 | −1.76 | 6 |

TABLE 17-continued

Pairwise Comparison of XB757 and 757

| Traits | XB757 | 757 | Range | # Loc. |
|---|---|---|---|---|
| Energy Values | | | | |
| TDN | 67.82 | 65.68 | 2.14 | 6 |
| NEL (Mcal/LB) | 0.68 | 0.66 | 0.02 | 6 |
| NFC % | 38.85 | 37.50 | 1.35 | 6 |
| Lbs CP/A | 1,354.67 | 1,474.91 | −120.24 | 6 |
| Lbs TDN/A | 11,019.01 | 11,942.15 | −923.14 | 6 |
| Lbs NEL/A | 11,097.71 | 11,935.90 | −838.19 | 6 |
| Lbs DDM/Ton | 1,533.00 | 1,435.80 | 97.20 | 6 |
| LBS CP/Ton | 169.87 | 162.33 | 7.54 | 6 |

*Summary over two years of data at 6 locations

TABLE 18

Description of Lines AR5751bm3, AR5152bm3 and AR5151bm3

AR5751bm3

COTYLEDON LEAF

| | |
|---|---|
| ANTHOCYANIN | PRESENT |
| LENGTH | 2–3 |

PLANT AND STALK

| | |
|---|---|
| PLANT HEIGHT | 5.5 ft. |
| EAR HEIGHT | 1.5 ft. |
| UNIFORMITY RATING | 7 |
| ANTHOCY. IN BRACE ROOTS | PRESENT |
| ANTHOCY. IN NODES | ABSENT |
| DIAM. AT 2nd NODE | 1.2 in. |
| ROOT RATING | EXCELLENT |

LEAVES

| | |
|---|---|
| ANGLE | UPRIGHT |
| COLOR | LIGHT GREEN |
| TOTAL NUMBER | 10–15 |
| NUMBER ABOVE EAR | 5–6 |
| LENGTH, EAR LEAF | 26 in. |
| MAX., WIDTH, EAR LEAF | 3.00 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | ABSENT |
| PLANT, TILLERING TASSEL | 0.00 |

TASSEL

| | |
|---|---|
| COMPACTNESS | AVERAGE |
| BRANCH ANGLE | 30–60 |
| NUMBER PRIMARY BRANCHES | >6 |
| SECONDARY BRANCH | ABSENT |
| LENGTH | 10–14 in. |
| TASSEL FERTILITY | 1 |
| SIZE RATING | 7 |
| TASSEL EXTENSION | PARTIALLY ENCLOSED |
| SHED IN BOOT? | NO |
| DIFFICULTY IN PULLING | AVERAGE |
| NUMBER LEAVES PULLED | 2 |
| ANTHER COLOR | YELLOW |
| GLUME COLOR  - TIP | LIGHT GREEN |
| - BASE | GREEN |
| - BAND | DARK GREEN |
| POLLEN SHED DURATION | N\A |
| POLLEN AMOUNT RATING | HEAVY |

EAR CHARACTERISTICS

| | |
|---|---|
| SILK COLOR | YELLOW |
| EAR LEAVES | ABSENT |

HUSK

| | |
|---|---|
| COVERAGE | LONG |
| LOOSENESS | N/A |
| EAR ANGLE RATING | 7 |
| SHANK LENGTH | 4–12 |
| EAR LENGTH | <6 |
| EAR SHAPE | CYLINDRICAL/CONICAL |
| UNIFORMITY | 7 |

KERNEL

| | |
|---|---|
| NO. ROWS | 16 |
| TYPE | DENT |
| SIZE | SMALL |
| BODY COLOR | ORANGE |
| CROWN COLOR | YELLOW |

COB

| | |
|---|---|
| COLOR | RED |
| DIAMETER MIDPOINT | 1–2 |

INSECT RESISTANCE

| | |
|---|---|
| ATTRACTIVE TO APHIDS | NO |

AR5152bm3

COTYLEDON LEAF

| | |
|---|---|
| ANTHOCYANIN | ABSENT |
| LENGTH | 2–3 |

PLANT AND STALK

| | |
|---|---|
| PLANT HEIGHT | 6.5 ft. |
| EAR HEIGHT | 2.5 ft. |
| UNIFORMITY RATING | 8 |
| ANTHOCY. IN BRACE ROOTS | PRESENT |
| ANTHOCY. IN NODES | ABSENT |
| DIAM. AT 2nd NODE | 1.3 in. |
| ROOT RATING | EXCELLENT |

LEAVES

| | |
|---|---|
| ANGLE | UPRIGHT |
| COLOR | MEDIUM |
| TOTAL NUMBER | 10–15 |
| NUMBER ABOVE EAR | 5–6 |
| LENGTH, EAR LEAF | 26 in. |
| MAX., WIDTH, EAR LEAF | 2.50 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | PRESENT |
| PLANT, TILLERING TASSEL | 0.00 |

TASSEL

| | |
|---|---|
| COMPACTNESS | AVERAGE |
| BRANCH ANGLE | 30–60 |
| NUMBER PRIMARY BRANCHES | 4–8 |
| SECONDARY BRANCH | PRESENT |
| LENGTH | 10–14 in. |
| TASSEL FERTILITY | 3 |
| SIZE RATING | 4 |
| TASSEL EXTENSION | PARTIALLY ENCLOSED |
| SHED IN BOOT? | NO |
| DIFFICULTY IN PULLING | EASY |
| NUMBER LEAVES PULLED | 2 |
| ANTHER COLOR | YELLOW |
| GLUME COLOR  - TIP | RED |
| - BASE | YELLOW |
| - BAND | DARK GREEN |
| POLLEN SHED DURATION | N\A |
| POLLEN AMOUNT RATING | LONG |

EAR CHARACTERISTICS

| | |
|---|---|
| SILK COLOR | YELLOW |
| EAR LEAVES | ABSENT |

HUSK

| | |
|---|---|
| COVERAGE | LONG |
| LOOSENESS | N/A |
| EAR ANGLE RATING | 7 |
| SHANK LENGTH | 4–12 |
| EAR LENGTH | <6 |
| EAR SHAPE | CYLINDRICAL |

TABLE 18-continued

Description of Lines AR5751bm3, AR5152bm3 and AR5151bm3

| | |
|---|---|
| UNIFORMITY | 8 |
| KERNEL | |
| | |
| NO. ROWS | 14 |
| TYPE | SEMI DENT |
| SIZE | AVERAGE |
| BODY COLOR | ORANGE |
| CROWN COLOR | YELLOW |
| COB | |
| | |
| COLOR | PINK |
| DIAMETER MIDPOINT | <1 |
| INSECT RESISTANCE | |
| | |
| ATTRACTIVE TO APHIDS | NO |
| AR5151bm3 | |
| COTYLEDON LEAF | |
| | |
| ANTHOCYANIN | PRESENT |
| LENGTH | 2–3 |
| PLANT AND STALK | |
| | |
| PLANT HEIGHT | 6.0 ft. |
| EAR HEIGHT | 2.0 ft. |
| UNIFORMITY RATING | 7 |
| ANTHOCY. IN BRACE ROOTS | DARK |
| ANTHOCY. IN NODES | ABSENT |
| DIAM. AT 2nd NODE | 1.0 in. |
| ROOT RATING | EXCELLENT |
| LEAVES | |
| | |
| ANGLE | HORIZONTAL |
| COLOR | LIGHT GREEN |
| TOTAL NUMBER | 10–15 |
| NUMBER ABOVE EAR | 5–6 |
| LENGTH, EAR LEAF | 26 in. |
| MAX., WIDTH, EAR LEAF | 2.50 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | ABSENT |
| PLANT, TILLERING TASSEL | 0.00 |
| TASSEL | |
| | |
| COMPACTNESS | AVERAGE |
| BRANCH ANGLE | 30–60 |
| NUMBER PRIMARY BRANCHES | 4–6 |
| SECONDARY BRANCH | ABSENT |
| LENGTH | 10–14 in. |
| TASSEL FERTILITY | 1 |
| SIZE RATING | 4 |
| TASSEL EXTENSION | PARTIALLY ENCLOSED |
| SHED IN BOOT? | NO |
| DIFFICULTY IN PULLING | AVERAGE |
| NUMBER LEAVES PULLED | 1 |
| ANTHER COLOR | YELLOW |
| GLUME COLOR  - TIP | RED |
|   - BASE | LIGHT GREEN |
|   - BAND | DARK GREEN |
| POLLEN SHED DURATION | N\A |
| POLLEN AMOUNT RATING | AVERAGE |
| EAR CHARACTERISTICS | |
| | |
| SILK COLOR | YELLOW |
| EAR LEAVES | ABSENT |
| HUSK | |
| | |
| COVERAGE | LONG |
| LOOSENESS | N/A |
| EAR ANGLE RATING | 7 |
| SHANK LENGTH | 4–12 |
| EAR LENGTH | <6 |
| EAR SHAPE | CYLINDRICAL |
| UNIFORMITY | 8 |
| KERNEL | |

TABLE 18-continued

Description of Lines AR5751bm3, AR5152bm3 and AR5151bm3

| | |
|---|---|
| NO. ROWS | 14 |
| TYPE | SEMI DENT |
| SIZE | AVERAGE |
| BODY COLOR | ORANGE |
| CROWN COLOR | YELLOW |
| COB | |
| | |
| COLOR | PINK |
| DIAMETER MIDPOINT | <1 |
| INSECT RESISTANCE | |
| | |
| ATTRACTIVE TO APHIDS | NO |

TABLE 19

| AR5751BM3 | |
|---|---|
| Slk Heat 1: | 1,441 |
| Slk Heat M: | 1,463 |
| Slk Heat F: | 1,505 |
| Slk Days 1: | 81 |
| Slk Days M: | 82 |
| Slk Days F: | 84 |
| Pol Heat 1: | 1,463 |
| Pol Heat M: | 1,485 |
| Pol Heat F: | 1,505 |
| Pol Days 1: | 82 |
| Pol Days M: | 83 |
| Pol Days F: | 84 |
| AR5152BM3 | |
| Slk Heat 1: | 1,587 |
| Slk Heat M: | 1,607 |
| Slk Heat F: | 1,633 |
| Slk Days 1: | 87 |
| Slk Days M: | 88 |
| Slk Days F: | 89 |
| Pol Heat 1: | 1,534 |
| Pol Heat M: | 1,564 |
| Pol Heat F: | 1,587 |
| Pol Days 1: | 85 |
| Pol Days M: | 86 |
| Pol Days F: | 87 |
| AR5151BM3 | |
| Slk Heat 1: | 1,256 |
| Slk Heat M: | 1,300 |
| Slk Heat F: | 1,345 |
| Slk Days 1: | 73 |
| Slk Days M: | 75 |
| Slk Days F: | 77 |
| Pol Heat 1: | 1,175 |
| Pol Heat M: | 1,231 |
| Pol Heat F: | 1,345 |
| Pol Days 1: | 70 |
| Pol Days M: | 72 |
| Pol Days F: | 77 |

TABLE 20

Description of Line AR5654bm3

| AR5654bm3 | |
|---|---|
| COTYLEDON LEAF | |
| | |
| ANTHOCYANIN | PRESENT |
| LENGTH | 2–3 |
| PLANT AND STALK | |
| | |
| PLANT HEIGHT | 6.0 ft. |
| EAR HEIGHT | 1.5 ft. |

TABLE 20-continued

Description of Line AR5654bm3

| | |
|---|---|
| UNIFORMITY RATING | 7 |
| ANTHOCY. IN BRACE ROOTS | PRESENT |
| ANTHOCY. IN NODES | ABSENT |
| DIAM. AT 2nd NODE | 1.1 in. |
| ROOT RATING | EXCELLENT |
| LEAVES | |
| ANGLE | HORIZONTAL |
| COLOR | MEDIUM |
| TOTAL NUMBER | 10–15 |
| NUMBER ABOVE EAR | >6 |
| LENGTH, EAR LEAF | 19 in. |
| MAX., WIDTH, EAR LEAF | 2.00 |
| ANTHOCYANIN, MARGIN | ABSENT |
| ANTHOCYANIN, SHEATH | ABSENT |
| PUBESCENCE, SHEATH | PRESENT |
| PUBESCENCE, MARGINS | ABSENT |
| PLANT, TILLERING TASSEL | 0.00 |
| TASSEL | |
| COMPACTNESS | LOOSE |
| BRANCH ANGLE | >60 |
| NUMBER PRIMARY BRANCHES | >8 |
| SECONDARY BRANCH | ABSENT |
| LENGTH | >14 in. |
| TASSEL FERTILITY | 1 |
| SIZE RATING | 6 |
| TASSEL EXTENSION | PARTIALLY ENCLOSED |
| SHED IN BOOT? | N/A |
| DIFFICULTY IN PULLING | EASY |
| NUMBER LEAVES PULLED | 2 |
| ANTHER COLOR | YELLOW |
| GLUME COLOR - TIP | RED |
| - BASE | LIGHT GREEN |
| - BAND | DARK GREEN |
| POLLEN SHED DURATION | N/A |
| POLLEN AMOUNT RATING | AVERAGE |
| EAR CHARACTERISTICS | |
| SILK COLOR | PINK |
| EAR LEAVES | ABSENT |
| HUSK | |
| COVERAGE | COVERS TIP |
| LOOSENESS | N/A |
| EAR ANGLE RATING | 6 |
| SHANK LENGTH | 4–12 |
| EAR LENGTH | <6 |
| EAR SHAPE | CYLINDRICAL |
| UNIFORMITY | 7 |
| KERNEL | |
| NO. ROWS | 14 |
| TYPE | FLINT |
| SIZE | SMALL |
| BODY COLOR | ORANGE |
| CROWN COLOR | YELLOW |
| COB | |
| COLOR | RED |
| DIAMETER MIDPOINT | <1 |
| INSECT RESISTANCE | |
| ATTRACTIVE TO APHIDS | NO |

TABLE 21

Description of Line AR5253bm3

| | |
|---|---|
| AR5253bm3 | |
| COTYLEDON LEAF | |
| ANTHOCYANIN | PRESENT |

TABLE 21-continued

Description of Line AR5253bm3

| | |
|---|---|
| LENGTH | 2–3 |
| PLANT AND STALK | |
| PLANT HEIGHT | 6.0 ft. |
| EAR HEIGHT | 2.5 ft. |
| UNIFORMITY RATING | 5 |
| ANTHOCY. IN BRACE ROOTS | PRESENT |
| ANTHOCY. IN NODES | ABSENT |
| DIAM. AT 2nd NODE | 1.1 in. |
| ROOT RATING | EXCELLENT |
| LEAVES | |
| ANGLE | UPRIGHT |
| COLOR | MEDIUM |
| TOTAL NUMBER | 10–15 |
| NUMBER ABOVE EAR | 5–6 |
| LENGTH, EAR LEAF | 25 in. |
| MAX., WIDTH, EAR LEAF | 3.00 |
| ANTHOCYANIN, MARGIN | ABSENT |
| ANTHOCYANIN, SHEATH | PRESENT |
| PUBESCENCE, SHEATH | PRESENT |
| PUBESCENCE, MARGINS | ABSENT |
| PLANT, TILLERING TASSEL | 0.00 |
| TASSEL | |
| COMPACTNESS | AVERAGE |
| BRANCH ANGLE | 30–60 |
| NUMBER PRIMARY BRANCHES | <4 |
| SECONDARY BRANCH | PRESENT |
| LENGTH | 10–14 in. |
| TASSEL FERTILITY | 3 |
| SIZE RATING | 4 |
| TASSEL EXTENSION | PARTIALLY ENCLOSED |
| SHED IN BOOT? | NO |
| DIFFICULTY IN PULLING | EASY |
| NUMBER LEAVES PULLED | 1 |
| ANTHER COLOR | YELLOW |
| GLUME COLOR - TIP | RED |
| - BASE | YELLOW |
| - BAND | DARK GREEN |
| POLLEN SHED DURATION | N\A |
| POLLEN AMOUNT RATING | AVERAGE |
| EAR CHARACTERISTICS | |
| SILK COLOR | YELLOW |
| EAR LEAVES | ABSENT |
| HUSK | |
| COVERAGE | COVERS TIP |
| LOOSENESS | N/A |
| EAR ANGLE RATING | 6 |
| SHANK LENGTH | 4–12 |
| EAR LENGTH | 6–9 |
| EAR SHAPE | CYLINDRICAL |
| UNIFORMITY | 8 |
| KERNEL | |
| NO. ROWS | 14 |
| TYPE | SEMI DENT |
| SIZE | AVERAGE |
| BODY COLOR | ORANGE |
| CROWN COLOR | YELLOW |
| COB | |
| COLOR | RED |
| DIAMETER MIDPOINT | 1–2 |
| INSECT RESISTANCE | |
| ATTRACTIVE TO APHIDS | NO |

TABLE 22

Description of Line AR5153bm3

| AR5153bm3 | |
|---|---|
| COTYLEDON LEAF | |
| ANTHOCYANIN | PRESENT |
| LENGTH | 2–3 |
| PLANT AND STALK | |
| PLANT HEIGHT | 6.0 ft. |
| EAR HEIGHT | 2.0 ft. |
| UNIFORMITY RATING | 6 |
| ANTHOCY. IN BRACE ROOTS | PRESENT |
| ANTHOCY. IN NODES | ABSENT |
| DIAM. AT 2nd NODE | 1.3 in. |
| ROOT RATING | EXCELLENT |
| LEAVES | |
| ANGLE | UPRIGHT |
| COLOR | MEDIUM |
| TOTAL NUMBER | 10–15 |
| NUMBER ABOVE EAR | 5–6 |
| LENGTH, EAR LEAF | 28 in. |
| MAX., WIDTH, EAR LEAF | 3.50 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | PRESENT |
| PLANT, TILLERING TASSEL | 0.00 |
| TASSEL | |
| COMPACTNESS | COMPACT |
| BRANCH ANGLE | <30 |
| NUMBER PRIMARY BRANCHES | 4–6 |
| SECONDARY BRANCH | PRESENT |
| LENGTH | 10–14 in. |
| TASSEL FERTILITY | 3 |
| SIZE RATING | 0 |
| TASSEL EXTENSION | PARTIALLY ENCLOSED |
| SHED IN BOOT? | YES |
| DIFFICULTY IN PULLING | EASY |
| NUMBER LEAVES PULLED | 2 |
| ANTHER COLOR | YELLOW |
| GLUME COLOR  - TIP | LIGHT GREEN |
| - BASE | LIGHT GREEN |
| - BAND | DARK GREEN |
| POLLEN SHED DURATION | N/A |
| POLLEN AMOUNT RATING | LONG |
| EAR CHARACTERISTICS | |
| SILK COLOR | YELLOW |
| EAR LEAVES | ABSENT |
| HUSK | |
| COVERAGE | LONG |
| LOOSENESS | N/A |
| EAR ANGLE RATING | 7 |
| SHANK LENGTH | <4 |
| EAR LENGTH | N/A |
| EAR SHAPE | N/A |
| UNIFORMITY | 0 |
| KERNEL | |
| NO. ROWS | N/A |
| TYPE | N/A |
| SIZE | N/A |
| BODY COLOR | N/A |
| CROWN COLOR | N/A |
| COB | |
| COLOR | N/A |
| DIAMETER MIDPOINT | N/A |
| INSECT RESISTANCE | |
| ATTRACTIVE TO APHIDS | NO |

TABLE 23

Description of Line AR5551bm3

| AR5551bm3 | |
|---|---|
| COTYLEDON LEAF | |
| ANTHOCYANIN | PRESENT |
| LENGTH | 2–3 |
| PLANT AND STALK | |
| PLANT HEIGHT | 5.5 ft. |
| EAR HEIGHT | 1.5 ft. |
| UNIFORMITY RATING | 7 |
| ANTHOCY. IN BRACE ROOTS | PRESENT |
| ANTHOCY. IN NODES | ABSENT |
| DIAM. AT 2nd NODE | 2.9 in. |
| ROOT RATING | EXCELLENT |
| LEAVES | |
| ANGLE | DROOPING |
| COLOR | MEDIUM |
| TOTAL NUMBER | 10–15 |
| NUMBER ABOVE EAR | 5–6 |
| LENGTH, EAR LEAF | 30 in. |
| MAX., WIDTH, EAR LEAF | 4.00 |
| ANTHOCYANIN, MARGIN | ABSENT |
| ANTHOCYANIN, SHEATH | ABSENT |
| PUBESCENCE, SHEATH | ABSENT |
| PUBESCENCE, MARGINS | PRESENT |
| PLANT, TILLERING TASSEL | 0.00 |
| TASSEL | |
| COMPACTNESS | LOOSE |
| BRANCH ANGLE | >60 |
| NUMBER PRIMARY BRANCHES | >8 |
| SECONDARY BRANCH | ABSENT |
| LENGTH | >14 in. |
| TASSEL FERTILITY | 1 |
| SIZE RATING | 6 |
| TASSEL EXTENSION | PARTIALLY ENCLOSED |
| SHED IN BOOT? | NO |
| DIFFICULTY IN PULLING | AVERAGE |
| NUMBER LEAVES PULLED | 1 |
| ANTHER COLOR | YELLOW |
| GLUME COLOR  - TIP | LIGHT GREEN |
| - BASE | LIGHT GREEN |
| - BAND | DARK GREEN |
| POLLEN SHED DURATION | N/A |
| POLLEN AMOUNT RATING | HEAVY |
| EAR CHARACTERISTICS | |
| SILK COLOR | YELLOW |
| EAR LEAVES | LOW |
| HUSK | |
| COVERAGE | SHORT |
| LOOSENESS | N/A |
| EAR ANGLE RATING | 5 |
| SHANK LENGTH | >12 |
| EAR LENGTH | 6–9 |
| EAR SHAPE | CYLINDRICAL |
| UNIFORMITY | 5 |
| KERNEL | |
| NO. ROWS | 16 |
| TYPE | SEMI DENT |
| SIZE | AVERAGE |
| BODY COLOR | ORANGE |
| CROWN COLOR | YELLOW |
| COB | |
| COLOR | WHITE |
| DIAMETER MIDPOINT | 1–2 |
| INSECT RESISTANCE | |
| ATTRACTIVE TO APHIDS | NO |

What is claimed is:

1. Inbred corn seed designated AR5651bm3 and having ATCC accession number 203350.

2. Hybrid corn seed produced from plants of a first inbred corn line, designated AR5651bm3 and having ATCC accession number 203350, and plants of a second inbred line that is homozygous for bm3.

3. An $F_1$ hybrid corn plant produced by:
   (a) planting and growing seeds of a first corn inbred line designated AR5651bm3 and represented by seed having ATCC accession number 203350, said seeds planted in pollinating proximity to seeds of a second inbred line that is homozygous for bm3;
   (b) preventing pollen production on plants resulting from either said first or said second inbred line seeds;
   (c) allowing cross pollination to occur between said plants of said inbred lines;
   (d) harvesting seeds produced on said plants of step (b); and
   (e) growing at least one harvested seed of step (d).

4. The hybrid corn plant of claim 3, wherein at step (b) said pollen production is prevented on said first corn inbred line AR5651bm3, represented by seed having ATCC accession number 203350.

5. The hybrid corn plant of claim 3, wherein at step (b), said pollen production is prevented on said second corn inbred line.

6. An $F_1$ hybrid corn seed produced by:
   (a) planting and growing seeds of a first corn inbred line AR5651bm3, represented by seed having ATCC accession number 203350, said seeds planted in pollinating proximity to seeds of a second inbred line that is homozygous for bm3;
   (b) preventing pollen production on plants resulting from either said first or said second inbred line seeds;
   (c) allowing cross pollination to occur between said plants of said inbred lines;
   (d) harvesting seeds produced on said plants of step (b).

7. The hybrid corn seed of claim 5, wherein at step (b), said pollen production is prevented on said first corn inbred line AR5651bm3, represented by seed having ATCC accession number 203350.

8. The hybrid corn seed of claim 6 wherein at step (b), said pollen production is prevented on said second corn inbred line.

* * * * *